(12) United States Patent
Inoue et al.

(10) Patent No.: US 10,010,376 B2
(45) Date of Patent: Jul. 3, 2018

(54) MEDICAL MANIPULATOR

(71) Applicant: OLYMPUS CORPORATION, Tokyo (JP)

(72) Inventors: Shintaro Inoue, Asaka (JP); Kosuke Kishi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 578 days.

(21) Appl. No.: 14/580,383

(22) Filed: Dec. 23, 2014

(65) Prior Publication Data

US 2015/0112362 A1    Apr. 23, 2015

Related U.S. Application Data

(63) Continuation of application No. PCT/JP2013/067397, filed on Jun. 25, 2013.

(30) Foreign Application Priority Data

Jul. 3, 2012    (JP) .................................. 2012-149340

(51) Int. Cl.
*B25J 17/00* (2006.01)
*A61B 34/00* (2016.01)
(Continued)

(52) U.S. Cl.
CPC .............. *A61B 34/70* (2016.02); *A61B 34/71* (2016.02); *A61B 2017/0034* (2013.01);
(Continued)

(58) Field of Classification Search
CPC . A61B 34/71; A61B 34/70; A61B 2090/0811; A61B 2090/062;
(Continued)

(56) References Cited

U.S. PATENT DOCUMENTS

2003/0040737 A1    2/2003    Merril et al.
2005/0228224 A1*   10/2005   Okada ................ A61B 1/00071
                                                    600/104
(Continued)

FOREIGN PATENT DOCUMENTS

JP          11056786 A      3/1999
JP          2005270171 A   10/2005

OTHER PUBLICATIONS

International Search Report dated Sep. 23, 2013 received in PCT/JP2013/067397.
(Continued)

*Primary Examiner* — Richard Louis
(74) *Attorney, Agent, or Firm* — Scully, Scott, Murphy & Presser, P.C.

(57) ABSTRACT

This medical manipulator includes a body section, an insertion section, a channel, a movement amount detection section configured to detect an amount of movement of a medical treatment tool inserted through a body-side channel provided in the body section, a distal-end-side contact section provided to be in contact with the medical treatment tool inserted through an insertion-side channel arranged in the insertion section and configured to rotate about its own axis to move the medical treatment tool, a first drive section configured to rotate the distal-end-side contact section. The distal-end-side contact section is rotated so as to move the medical treatment tool with respect to the insertion-side channel by an amount of movement which is the same as the amount of movement detected by the movement amount detection section.

6 Claims, 7 Drawing Sheets

(51) Int. Cl.
    *A61B 17/00*    (2006.01)
    *A61B 34/30*    (2016.01)
    *A61B 90/00*    (2016.01)
(52) U.S. Cl.
    CPC ............ *A61B 2017/00296* (2013.01); *A61B 2034/301* (2016.02); *A61B 2090/062* (2016.02); *A61B 2090/067* (2016.02); *A61B 2090/0811* (2016.02)
(58) Field of Classification Search
    CPC ........ A61B 2034/301; A61B 2090/067; A61B 2017/0034; A61B 2017/00296
    See application file for complete search history.

(56) References Cited

U.S. PATENT DOCUMENTS

| | | | |
|---|---|---|---|
| 2009/0018390 A1* | 1/2009 | Honda | ............... A61B 1/00059 600/106 |
| 2010/0016666 A1 | 1/2010 | Hasegawa | |
| 2010/0022825 A1 | 1/2010 | Yoshie | |
| 2010/0048992 A1 | 2/2010 | Okada et al. | |

OTHER PUBLICATIONS

Extended Supplementary European Search Report dated Feb. 15, 2016 from related European Application No. 13 81 3606.4.

\* cited by examiner

MEDICAL MANIPULATOR

FIELD OF THE INVENTION

The present invention relates to a medical manipulator in which a flexible medical treatment tool is inserted. This application is a continuation application based on PCT Patent Application No. PCT/JP2013/067397, filed Jun. 25, 2013, claiming priority based on Japanese Patent Application No. 2012-149340, filed Jul. 3, 2012, the content of which is incorporated herein by reference.

DESCRIPTION OF RELATED ART

Medical treatment tools include flexible medical treatment tools which easily bend according to use of a user or the like and hard medical treatment tools which do not bend in normal treatment. Flexible medical treatment tools and hard medical treatment tools are appropriately used depending on a procedure. A treatment device e.g., a medical manipulator or an endoscope system, which is used by inserting the flexible medical treatment tool into an internally formed channel is considered in order to use an existing flexible medical treatment tool as if it were a hard medical treatment tool.

For example, in the endoscope system disclosed in Japanese Unexamined Patent Application, First Publication No. 2005-270171, a flexible insertion section is provided on a distal end of an operation section (body section) to be operated by an operator. A medical treatment tool channel is formed from a distal end of the insertion section to a proximal end of the operation section.

A medical treatment tool housing device is mounted on the proximal end of the insertion section via a medical treatment tool insertion/removal device. The medical treatment tool insertion/removal device has a housing fixed to a proximal-end side of the operation section. Within the housing, a pair of rollers are disposed at the housing so as to sandwich the medical treatment tool insertion section of the medical treatment tool. A rotation shaft of each roller is supported rotatably by a roller support section which is a frame. A motor is connected to each roller via a transfer mechanism and can rotate the roller in a desired direction.

In addition, the roller support section is supported by the rotation shaft to be rotatable with respect to the housing. Thus, by rotating the rotation shaft using the motor, it is possible to perform rotation of an orientation in which the roller support section or the pair of rollers are disposed.

That is, by switching an orientation in which the roller support section is disposed, it is possible to perform switching between a mode in which the pair of rollers advance or retract the medical treatment tool insertion section which is inserted through the medical treatment tool channel with respect to the medical treatment tool channel by using an electromotive force and a mode in which the medical treatment tool insertion section is rotated about the axis of the medical treatment tool channel.

In general, the insertion section is formed to be elongate to minimize the number of internal components or a size so that the insertion section can be inserted into a test object. On the other hand, the operation section is formed to be thicker (larger) than the insertion section that components which are not housed in the insertion section can be arranged therein.

SUMMARY OF THE INVENTION

According to a first aspect of the present invention, a medical manipulator including: a body section; an elongate insertion section having a proximal-end portion connected to the body section; a channel through which a flexible medical treatment tool is able to be inserted and configured to communicate with a distal-end opening formed in a distal-end section of the insertion section and communicate with a proximal-end opening formed in the body section; a movement amount detection section configured to detect an amount of movement of the medical treatment tool, which is inserted through a body-side channel which is a portion provided in the body section in the channel, for the body-side channel of the medical treatment tool; a distal-end-side contact section provided to be in contact with the medical treatment tool inserted through an insertion-side channel which is a portion provided in the insertion section in the channel and configured to rotate about its own axis to move the medical treatment tool to the insertion-side channel; and a first drive section provided on the body section and configured to rotate the distal-end-side contact section. The distal-end-side contact section is rotated so as to move the medical treatment tool with respect to the insertion-side channel by an amount of movement which is the same as the amount of movement that has been detected by the movement amount detection section.

According to a second aspect of the present invention, the medical manipulator according to the first aspect may further include: a wire configured to rotate the distal-end-side contact section. The first drive section may have an output shaft configured rotate to transfer a driving force, and the wire may be wound around the output shaft and connected to the distal-end-side contact section.

According to a third aspect of the present invention, the medical manipulator according to the second aspect may further include: a proximal-end-side contact section which is capable of contacting with the medical treatment tool inserted through the body-side channel and which rotates about its own axis to move the medical treatment tool with respect to the body-side channel The first drive section may rotate the proximal-end-side contact section.

According to a fourth aspect of the present invention, the medical manipulator according to the third aspect may further include: an output branch mechanism configured to transfer part of the driving force about the axis of the output shaft as a driving force about the axis of an auxiliary output shaft having the axis intersecting the axis of the output shaft. The output shaft may be disposed in parallel to an axis of the channel, the wire may be wound around the auxiliary output shaft and connected to the distal-end-side contact section, the amounts of movements may be an amount of movement about the axis of the channel, an axis of the proximal-end-side contact section may be disposed in parallel to the axis of the channel, and the proximal-end-side contact section may be rotated by the driving force transferred to the output shaft.

According to a fifth aspect of the present invention, the medical manipulator according to the first or second aspect may further include: a proximal-end-side contact section which is capable of contacting with the medical treatment tool inserted through the body-side channel and which rotates about its own axis to move the medical treatment tool with respect to the body-side channel; a second drive section provided on the body section and configured to rotate the proximal-end-side contact section; and a drive amount adjustment section adjusting a drive amount of the first drive section for rotating the distal-end-side contact section based on a result of detecting the amount of movement, that has been detected by the movement amount detection section. When the proximal-end-side contact section is rotated by the second drive section, the movement amount detection section may transmit the result of detecting the amount of movement to the drive amount adjustment section and the drive amount adjustment section may adjust the drive amount of the first drive section based on the detection result such that the amount of movement of the medical treatment tool with respect to the insertion-side channel is equal to the amount of movement of the medical treatment tool with respect to the body-side channel.

According to a sixth aspect of the present invention, in the medical manipulator according to any one of the first to third and fifth aspects, the amounts of movements may be an amount of movement in an axial direction of the channel, and the distal-end-side contact section may be disposed so as to rotate on a reference plane including the axis of the channel.

According to a seventh aspect of the present invention, in the medical manipulator according to any one of the first to third and fifth aspects, the amount of movement may be an amount of movement about the axis of the channel, and the distal-end-side contact section may be disposed so as to rotate about an axis parallel to the axis of the channel.

DETAILED DESCRIPTION OF THE PREFERRED EMBODIMENTS (First Embodiment)

Hereinafter, the first embodiment of a medical manipulator 1 according to the present invention will be described with reference to FIGS. 1 and 2.

Figure 1:
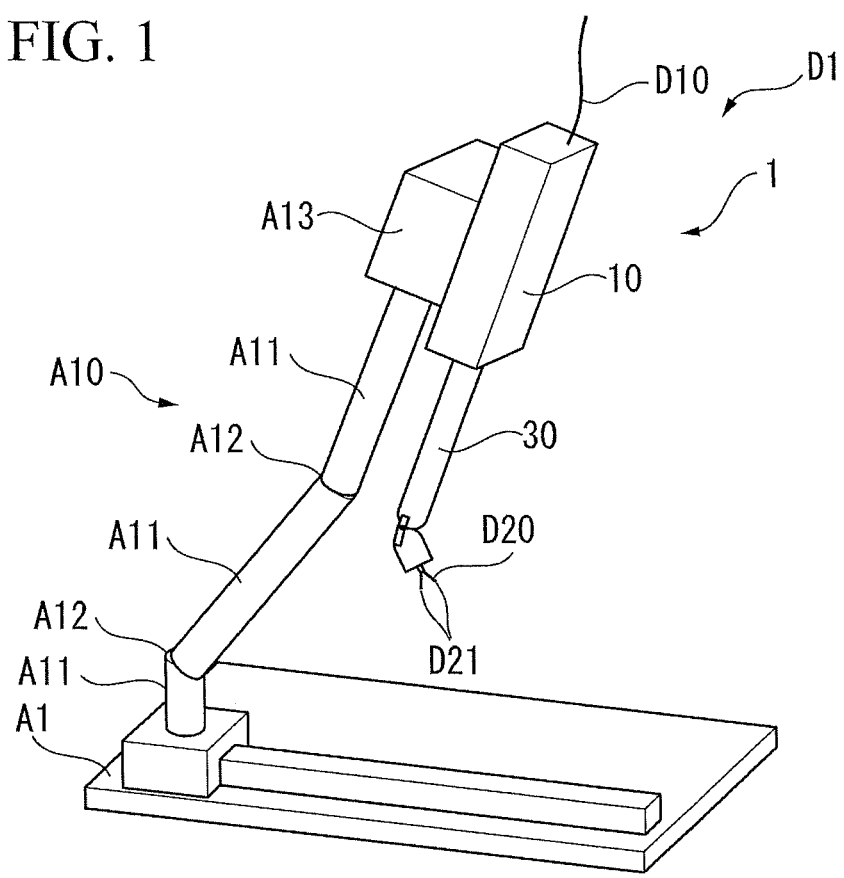
FIG. 1 is a perspective view illustrating a state in which a medical manipulator according to a first embodiment of the present invention is mounted on an arm.

As shown in FIG. 1, this medical manipulator 1, for example, is mounted on a distal end of an arm A10, and is used with inserting a flexible medical treatment tool Dl formed of a flexible material into an internally formed channel 41 (see FIG. 2) to be described later.

The arm A10 is mutually rotatably connected to an end portion of a rod A11 disposed on a base A1 via a joint portion A12. A holding section A13 is fixed to a distal end of the arm A10, i.e., an end portion of the rod A11. A body section 10 of the medical manipulator 1 to be described later is detachably mounted on the holding section A13 by an attachment/detachment mechanism (not shown).

Here, the medical treatment tool D1 will be described. A medical treatment tool having a well-known configuration is used as the medical treatment tool D1. The medical treatment tool D1 includes a medical treatment tool insertion section D10, a treatment section D20, and a medical treatment tool operation section (not shown). The medical treatment tool insertion section D10 is formed of material that is softer and more flexible than a metal, such as a resin. The treatment section D20 is provided on a distal-end section of the medical treatment tool insertion section D10 to perform a treatment such as grasping. The medical treatment tool operation section is provided on a proximal-end portion of the medical treatment tool insertion section D10 to operate the treatment section D20. A concave section extending in a longitudinal direction of the medical treatment tool insertion section D10 is formed on an outer surface of the medical treatment tool insertion section D10.

In the embodiment, a grasping forceps is used as the medical treatment tool D1. In the medical treatment tool D1, a pair of forceps pieces D21 that can be opened/closed by operating the medical treatment tool operation section are provided in the treatment section D20. However, the medical treatment tool D1 is not limited to the grasping forceps, and a desired medical treatment tool can be used as long as the medical treatment tool is flexible.

Figure 2:
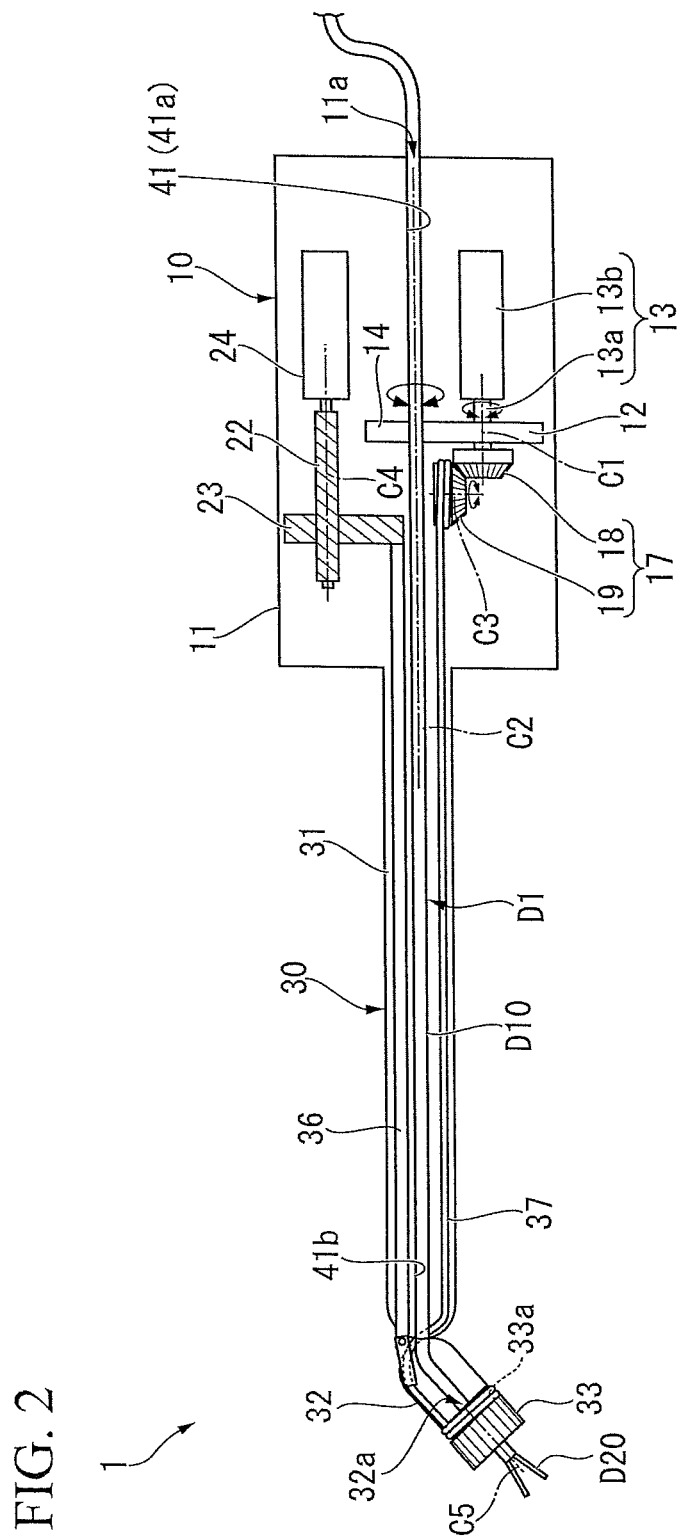
FIG. 2 is a cross-sectional view of schematic main parts in a plane of the medical manipulator according to the first embodiment of the present invention.

As shown in FIGS. 1 and 2, the medical manipulator 1 includes a body section 10 and an insertion section 30. The insertion section 30 is formed to be more elongate than the body section 10 and has a proximal-end portion connected to the body section 10.

As shown in FIG. 2, the body section 10 includes a casing 11, a body-side medical treatment tool rotating roller (proximal-end-side contact section or movement amount detection section) 12, and a drive motor (first drive section) 13. The body-side medical treatment tool rotating roller 12 is housed in the casing 11. The drive motor 13 is coaxially connected to the body-side medical treatment tool rotating roller 12.

Inside the body section 10 and the insertion section 30, the above-described channel 41 is formed by a pipe material (not shown) or the like. The channel 41 communicates with each of a distal-end opening 32a formed on a distal-end side of the insertion section 30 and a proximal-end opening 11a formed in the casing 11. In the channel 41, a portion arranged in the body section 10 is referred to as a "body-side channel 41a" and a portion arranged in the insertion section 30 is referred to as an "insertion-side channel 41b." In the channel 41 (body-side channel 41a), a through hole (not shown) is formed in a portion in which the body-side medical treatment tool rotating roller 12 and the support roller 14 to be described later are provided. The through hole communicates with an internal space of the casing 11. The above-described medical treatment tool D1 can be inserted into the channel 41, and the medical treatment tool insertion section D10 of the medical treatment tool D1 is inserted into the channel 41.

The body-side medical treatment tool rotating roller 12 is formed in a disc shape, and an axis C1 of the body-side medical treatment tool rotating roller 12 is disposed in parallel to an axis C2 of the channel 41. It is preferable that anti-slip working such as the formation of a micro groove extending in parallel to the axis C1 of the body-side medical treatment tool rotating roller 12 or the like is performed on a side surface of the body-side medical treatment tool rotating roller 12.

The side surface of the body-side medical treatment tool rotating roller 12 is disposed to be in contact with a side surface of the medical treatment tool insertion section D10 of the medical treatment tool D1 inserted through the body-side channel 41a via the through hole formed in the channel 41.

A distal-end section of an output shaft 13a of the drive motor 13 is fixed to the proximal end of the body-side medical treatment tool rotating roller 12. A motor body 13b of the drive motor 13 is fixed to the casing 11, and the output shaft 13a rotates about the axis C1 of the body-side medical treatment tool rotating roller 12 by a driving force generated by the motor body 13b. Thereby, the driving force generated by the motor body 13b can be transferred to the body-side medical treatment tool rotating roller 12 via the output shaft 13a to cause the body-side medical treatment tool rotating roller 12 to rotate about the axis C1.

In the embodiment, by rotating the body-side medical treatment tool rotating roller 12 about the axis C1 of the body-side medical treatment tool rotating roller 12, the medical treatment tool D1 in contact with a side surface of the body-side medical treatment tool rotating roller 12 rotates about the axis C2 of the medical treatment tool D1 with respect to the body-side channel 41a. That is, the amount of movement of the medical treatment tool D1 with respect to the body-side channel 41a is the amount of rotation (an angle of rotation; hereinafter referred to as an "amount of rotational movement") about the axis C2 of the medical treatment tool D1. The body-side medical treatment tool rotating roller 12 also functions as a movement amount detection section for detecting the amount of rotational movement about the axis C2 of the medical treatment tool D1 inserted through the body-side channel 41a.

Within the casing 11, the support roller 14 is disposed within the casing 11 such that the medical treatment tool insertion section D10 of the medical treatment tool D1 is sandwiched between the support roller 14 and the body-side medical treatment tool rotating roller 12. The support roller 14 is supported rotatably by the casing 11. The body-side medical treatment tool rotating roller 12 and the support roller 14 come in contact with each other from both sides of a radial direction of the medical treatment tool insertion section D10 inserted through the body-side channel 41a, and therefore the medical treatment tool insertion section D10 is prevented from slipping in a circumferential direction of the body-side medical treatment tool rotating roller 12 with respect to the body-side medical treatment tool rotating roller 12.

An output branch mechanism 17 is connected to the distal-end section of the body-side medical treatment tool rotating roller 12. Specifically, the output branch mechanism 17 has a first gear 18 and a second gear (auxiliary output shaft) 19. The first gear 18 is fixed to a distal end of the body-side medical treatment tool rotating roller 12. The second gear 19 engages with the first gear 18. The gears 18 and 19 are so-called bevel gears. The first gear 18 is fixed to the body-side medical treatment tool rotating roller 12 so that its own axis is consistent with the axis C1 of the body-side medical treatment tool rotating roller 12. On the other hand, in a plan view, the second gear 19 is supported rotatably by the casing 11 so that its own axis C3 is orthogonal to the axis C1 of the body-side medical treatment tool rotating roller 12. That is, the gears 18 and 19 which engage with each other convert part of the driving force of the motor body 13b transferred from the output shaft 13a of the drive motor 13 into a driving force about the axis C3 of the second gear 19 from the driving force about the axis C1 of the body-side medical treatment tool rotating roller 12 and transfer the converted driving force.

A worm 22 is disposed within the casing 11 so as to extend in parallel to the axis C1 of the body-side medical treatment tool rotating roller 12. The worm 22 and a worm wheel 23 engaging with the worm 22 are rotatably supported within the casing 11. A swing motor 24 is connected to a proximal end portion of the worm 22. The swing motor 24 is connected to the casing 11. The swing motor 24 rotates the worm 22 about an axis C4 of the worm 22, thereby the worm wheel 23 can be moved with respect to the worm 22 in the direction of the axis C1 of the body-side medical treatment tool rotating roller 12.

The insertion section 30 includes an insertion-section body 31, a swing member 32, and a rotation member (distal-end-side contact section) 33. The insertion-section body 31 is a pipe-like member fixed to a distal-end surface of the casing 11 and extending in the direction of the axis C2 of the channel 41. The swing member 32 is connected to the distal-end section of the insertion-section body 31 in a swingable manner. A rotation member 33 is supported by the swing member 32 to be rotatable about the axis C5 (hereinafter referred to as the "axis C5 of the rotation member 33") parallel to a normal line of a distal-end surface of the swing member 32.

Although not shown, a shaft member is provided in one of the insertion-section body 31 and the swing member 32, and a hole engaging with the shaft member to be relatively movable about the shaft member is formed in the other. Through this configuration, the swing member 32 is connected to the distal-end section of the insertion-section body 31 in a swingable manner.

A bearing is provided on the distal-end surface of the swing member 32, and the swing member 32 is supported so that the rotation member 33 is rotatable about the axis C5 of the rotation member 33.

An insertion-side channel 41b is formed in the insertion-section body 31 and the swing member 32. The insertion-side channel 41b is a portion arranged in the insertion section 30 of the channel 41, The insertion-side channel 41b communicates with the above-described distal-end opening 32a formed in the distal-end surface of the swing member 32.

In the rotation member 33, although not shown, a through hole communicating with the channel 41 is formed on the axis C2 of the channel 41. On an inner circumferential surface of the through hole, a protrusion section protruding from the inner circumferential surface is provided. The medical treatment tool D1 is inserted through an insertion-side channel 41b so that the treatment section D20 protrudes in the front of the rotation member 33. This protrusion section engages (comes in contact) with a concave section formed in a side surface of the medical treatment tool insertion section D10 and therefore the rotation about the axis C2 of the medical treatment tool D1 for the insertion-side channel 41b is regulated. The size of the protrusion section is set so that a predetermined frictional force occurs between the protrusion section and the side surface of the medical treatment tool insertion section D10 even when the medical treatment tool D1 is moved in the direction of the axis C2 of the medical treatment tool D1 with respect to the channel 41.

The rotation member 33 is disposed so that the axis C5 of the rotation member 33 coincides with the axis C2 of the channel 41.

In the embodiment, a member formed of a material such as a metal and formed in substantially a pipe shape is used as the insertion-section body 31, the swing member 32, and the rotation member 33. That is, the insertion section 30 according to the embodiment is a so-called hard insertion section.

A connecting rod 36 is inserted through a pipeline of the insertion-section body 31. The distal-end section of the connecting rod 36 is mounted on the swing member 32 at a position shifted in a direction orthogonal to the axis C2 of the channel 41 with respect to a swing center of the swing member 32 in a plan view. The proximal-end portion of the connecting rod 36 is mounted on the worm wheel 23. Because of this, the swing motor 24 can swing the swing member 32 by moving the worm wheel 23 in the direction of the axis C1 of the body-side medical treatment tool rotating roller 12.

An operation wire (wire) 37 formed linearly is inserted through the pipeline of the insertion-section body 31. The distal-end side of the operation wire 37 is connected to the rotation member 33 in a state in which the distal-end side of the operation wire 37 is wound around a proximal-end portion 33*a* of the rotation member 33. On the other hand, the proximal-end side of the operation wire 37 is wound around an outer circumferential surface of the second gear 19. The operation wire 37 is preferably used being inserted into a guide tube in order to stabilize the motion of the operation wire 37.

Through this configuration, by rotating the second gear 19 about the axis C3 of the second gear 19 by the drive motor 13, the rotational force of the second gear 19 can be transferred via the operation wire 37, and the rotation member 33 can rotate about its own axis C5. Then, it is possible to rotate the medical treatment tool insertion section D10 of the medical treatment tool D1 inserted through the through hole of the rotation member 33 with respect to the insertion-side channel 41*b*.

Since the operation wire 37 having a small outer diameter is used for the transfer of the driving force between the second gear 19 and the rotation member 33, the outer diameter of the insertion section 30 is not necessary to increase.

As described above, it is possible to rotate the body-side medical treatment tool rotating roller 12 and the rotation member 33 by driving the drive motor 13. The outer diameter of the proximal-end portion 33*a* of the rotation member 33 for winding the operation wire 37 is set as follows. That is, the outer diameter of the proximal-end portion 33*a* is set such that both an amount of rotational movement of a rotation of the body-side medical treatment tool rotating roller 12 at the proximal-end side of the medical treatment tool insertion section D10, and an amount of rotational movement of the rotation member 33 at the distal-end side of the medical treatment tool insertion section D10, which are caused by driving the drive motor 33, are set to be the same as each other. In this manner, the proximal-end portion 33*a* of the rotation member 33 functions as a drive amount adjustment section.

An electric contact point (not shown) provided on an outer surface of the casing 11 is connected to an electric contact point provided in the holding section A13. Control of the drive motor 13 and the swing motor 24 is configured to be performed from an operation section (not shown) provided on a base A1 via these electric contact points.

Next, a motion of the medical manipulator 1 configured as above will be described. Here, the case in which treatment is performed by inserting the medical manipulator 1 into a body cavity of a patient will be described.

A user mounts the body section 10 of the medical manipulator 1 on the holding section A13 of the arm A10. Then, the insertion section 30 of the medical manipulator 1 is introduced into the body cavity through a trocar mounted on the patient. Under observation through an endoscope, the swing motor 24 is driven and an orientation of the swing member 32 with respect to the insertion-section body 31 is adjusted by operating the operation section if necessary. The distal-end section of the insertion section 30 is caused to face a target tissue which is a treatment target.

The flexible medical treatment tool D1 such as a grasping forceps is inserted from the proximal-end opening 11*a* of the medical manipulator 1 to the channel 41. The treatment section D20 of the medical treatment tool D1 is protruded in front of the rotation member 33, and a protrusion section of the rotation member 33 is caused to engage with a concave section of the medical treatment tool insertion section D10.

When it is necessary to adjust the orientation of the treatment section D20 about the axis C2 with respect to the target tissue, the user drives the drive motor 13 by operating the operation section. Thereby, the body-side medical treatment tool rotating roller 12 rotates about the axis C1 and the rotation member 33 rotates about its own axis C5. At this time, the amount of rotation of the body-side medical treatment tool rotating roller 12 and the amount of rotation of the rotation member 33 are adjusted as described above. As the result, in the medical treatment tool insertion section D10, the amount of rotational movement about the axis C1 of the body-side medical treatment tool rotating roller 12 is the same in the proximal-end side and the distal-end side.

Since the medical treatment tool insertion section D10 is rotated at two positions of the direction of the axis C1 of the body-side medical treatment tool rotating roller 12, twisting of the medical treatment tool D1 is suppressed even in the flexible medical treatment tool D1.

By the user pushes the medical treatment tool D1 to the medical manipulator 1 or pulls from the medical manipulator 1, an amount of protrusion in which the treatment section D20 protrudes from the rotation member 33 can be adjusted against a frictional force generated between the protrusion section of the rotation member 33 and the medical treatment tool insertion section D10.

The treatment section D20 of the medical treatment tool D1 grasps the target tissue by operating the medical treatment tool operation section and performs a necessary treatment. Subsequently, the medical treatment tool D1 is pulled out of the medical manipulator 1. The insertion section 30 of the medical manipulator 1 is pulled out of the trocar and the trocar is removed from the patient. Thereafter, necessary treatment such as suturing of an opening of the patient is performed and a series of procedures end.

As described above, according to the medical manipulator 1 according to the embodiment, the body-side medical treatment tool rotating roller 12 detects an amount of rotational movement of the proximal-end side of the medical treatment tool insertion section D10 in which the medical treatment tool insertion section D10 has rotated within the body-side channel 41*a*. Then, the distal-end side of the medical treatment tool insertion section D10 is rotated along with the rotation member 33 with respect to the insertion-side channel 41*b* so that the amount of rotational movement thereof is the same as the detected amount of rotational movement. As the result, the proximal-end side and the distal-end side of the medical treatment tool insertion section D10 are possible to similarly rotate with respect to the channel 41 even when the flexible medical treatment tool D1 is used.

The medical manipulator 1 according to the embodiment is configured to include the body-side medical treatment tool rotating roller 12 in contact with the side surface of the proximal-end side of the medical treatment tool insertion section D10 and is configured to rotate the body-side medical treatment tool rotating roller 12 through the drive motor 13. Accordingly, the drive motor 13 can automatically rotate the proximal-end side as well as the distal-end side of the medical treatment tool insertion section D10. As the result, it is possible to reduce a burden on the user who operates the medical treatment tool D1.

The medical manipulator 1 according to the embodiment distributes a driving force generated by the drive motor 13 to a force about the body-side medical treatment tool rotating roller 12 and the force about the second gear 19, in which orientations of rotation axes are different from each other, by the output branch mechanism 17. That is, the distal-end side and the proximal-end side of the medical treatment tool insertion section D10 are rotated by the driving force generated by the drive motor 13. Thereby, the distal-end side and the proximal-end side of the medical treatment tool insertion section D10 can be rotated together by one drive motor 13. Therefore, it is possible to reduce the number of motors necessary to configure the medical manipulator 1.

The axis C1 of the body-side medical treatment tool rotating roller 12 is disposed in parallel to the axis C2 of the channel 41. As the result, the driving force about the axis C1 of the body-side medical treatment tool rotating roller 12 transferred to the body-side medical treatment tool rotating roller 12 can be effectively transferred as the driving force for rotating the medical treatment tool insertion section D10 about the axis C2 of the channel 41.

In the medical manipulator 1 according to the embodiment, since an operation wire 37 is used for transferring the driving force between the second gear 19 and the rotation member 33, it is possible to minimize the outer diameter of the insertion section 30.

In the medical manipulator 1 according to the embodiment, the rotation member 33 rotates about its own axis C5, thereby the medical treatment tool D1 engaging with the rotation member 33 can be rotated about the axis C2 of the channel 41 and the orientation of the treatment section D20 about the axis C2 with respect to the insertion-side channel 41b can be adjusted.

In the embodiment, when driving the drive motor 13, the amount of rotational movement of the body-side medical treatment tool rotating roller 12 at the proximal-end side of the medical treatment tool insertion section D10 is set to be consistent with the amount of rotational movement in which the rotation member 33 rotates about its own axis C5 by adjusting the outer diameter of the proximal-end portion 33a of the rotation member 33. However, this adjustment, for example, can be performed by adjusting the outer diameter of the body-side medical treatment tool rotating roller 12 or the outer diameter (the number of teeth) of the second gear 19 without being limited to the proximal-end portion 33a. In this case, the body-side medical treatment tool rotating roller 12 or the second gear 19 serves as a drive amount adjustment section.

In the embodiment, a configuration in which a concave section is formed in the medical treatment tool insertion section D10 and a protrusion section engaging with the concave section is formed in the rotation member 33 is assumed. However, the concave section and the protrusion section need not be formed.

(Second Embodiment)

Next, the second embodiment of the present invention will be described with reference to FIG. 3. The same portions as those of the first embodiment are assigned the same reference signs, a description thereof will be omitted, and only different points will be described.

Figure 3:
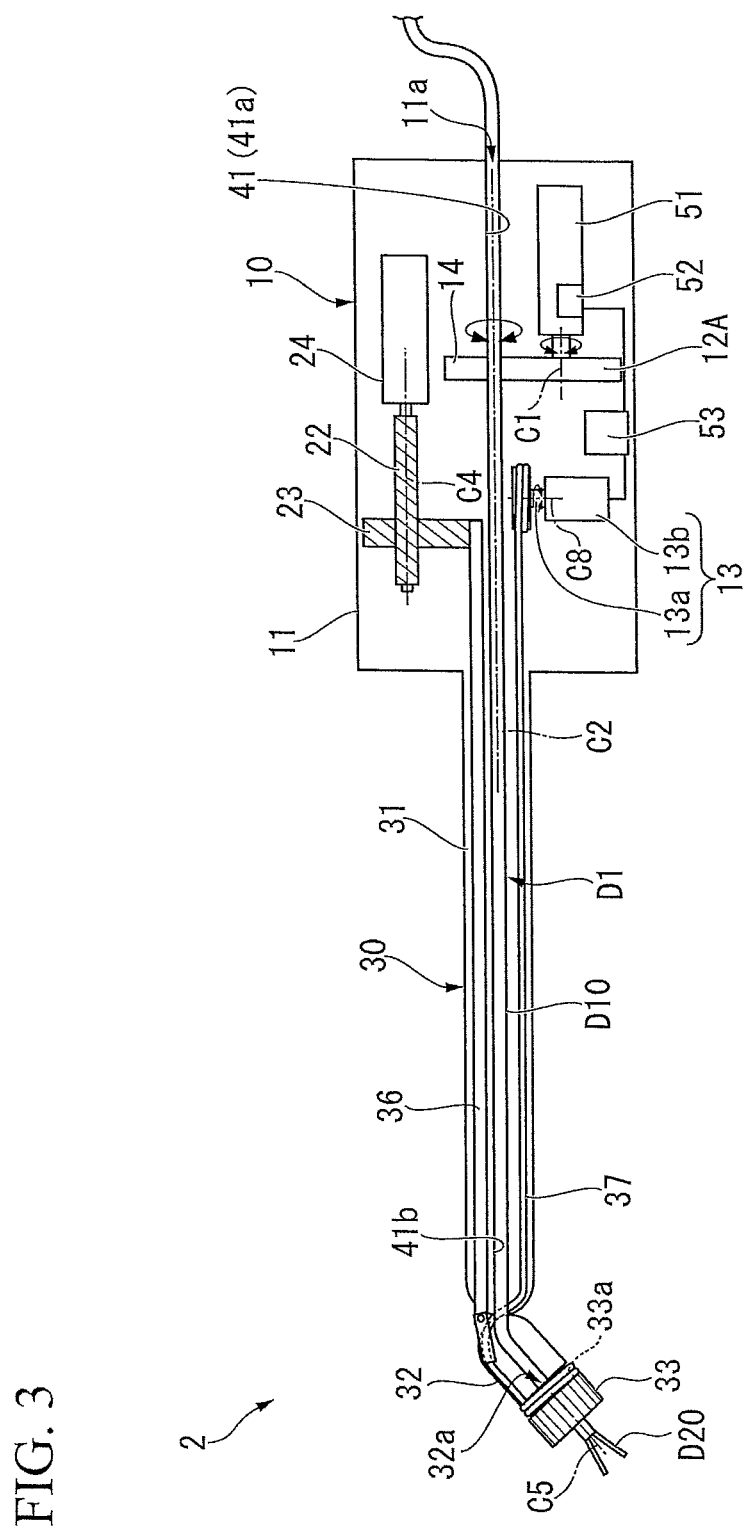
FIG. 3 is a cross-sectional view of schematic main parts in a plane of a medical manipulator according to a second embodiment of the present invention.

As shown in FIG. 3, a medical manipulator 2 according to the embodiment includes a second drive motor (second drive section) 51, an encoder (movement amount detection section) 52, and a drive amount control section (drive amount adjustment section) 53 instead of the output branch mechanism 17 of the medical manipulator 1 according to the first embodiment. A body-side medical treatment tool rotating roller 12A in the embodiment has the same configuration as the body-side medical treatment tool rotating roller 12 according to the first embodiment. However, the body-side medical treatment tool rotating roller 12A in the embodiment does not function as the movement amount detection section according to the first embodiment.

The second drive motor 51 is housed within the casing 11 and fixed to the surface of the proximal-end side of the body-side medical treatment tool rotating roller 12A. The second drive motor 51 can rotate the medical treatment tool rotating roller 12A about its own axis C1.

An encoder having a well-known configuration can be used as the encoder 52. The encoder 52 detects an amount of rotation of the rotation axis of the second drive motor 51 and transmits a result of detecting the amount of rotation to the drive amount control section 53.

The amount of rotation of the rotation shaft and the amount of rotational movement about the axis C2 of the medical treatment tool D1 have a proportional relation. As the result, the encoder 52 can substantially detect the amount of rotational movement of the medical treatment tool D1.

In the embodiment, the drive motor 13 is disposed so that an axis C8 of an output shaft 13a is orthogonal to the axis C2 of the channel 41 in a plan view. The proximal-end side of the operation wire 37 is wound around an outer circumferential surface of the output shaft 13a.

The drive amount control section 53 includes a calculation element and a memory (not shown). The memory stores a constant representing the necessary number of rotations of the output shaft 13a of the drive motor 13 when the rotation axis of the second drive motor 51 rotates one rotation such that the amount of rotational movement of the body-side medical treatment tool rotating roller 12A at the proximal-end side of the medical treatment tool insertion section D10 and the amount of rotational movement about the axis C5 of the rotation member 33 are equal to each other.

The calculation element performs a calculation operation of multiplying the detection result transmitted from the encoder 52 by the above-described constant. By applying a voltage according to the calculation result to the drive motor 13, the rotational speed of the output shaft 13a is adjusted and the rotation member 33 is rotated by the drive motor 13.

According to the medical manipulator 2 according to the embodiment configured in this manner, the distal-end side of the medical treatment tool D1 is possible to be rotated similarly to the proximal-end side of the flexible medical treatment tool D1 inserted through the channel 41 when the proximal-end side of the flexible medical treatment tool D1 is rotated.

Further, the medical manipulator 2 according to the embodiment includes the body-side medical treatment tool rotating roller 12A, the second drive motor 51, the encoder 52, and the drive amount control section 53. Because of this, the two drive motors 13 and 51 can rotate the distal-end side and the proximal-end side of the medical treatment tool D1 with higher accuracy.

Since the operation wire 37 is used for transfer the driving force between the output shaft 13a and the rotation member 33, it is possible to reduce a size the outer diameter of the insertion section 30.

In the embodiment, the encoder for detecting the amount of rotation of the rotation axis of the drive motor 13 may be included and the detection result by the encoder may be transmitted to the drive amount control section 53. In this case, the calculation element of the drive amount control section 53 receives a real amount of rotation of the drive motor 13 and performs feedback control so that the amounts of rotational movement in the proximal-end side and the distal-end side of the medical treatment tool insertion section D10 are equal to each other.

(Third Embodiment)

Next, the third embodiment of the present invention will be described with reference to FIG. 4. The same portions as those of the above-described embodiment are assigned the same reference signs, description thereof will be omitted, and only different points will be described.

Figure 4:
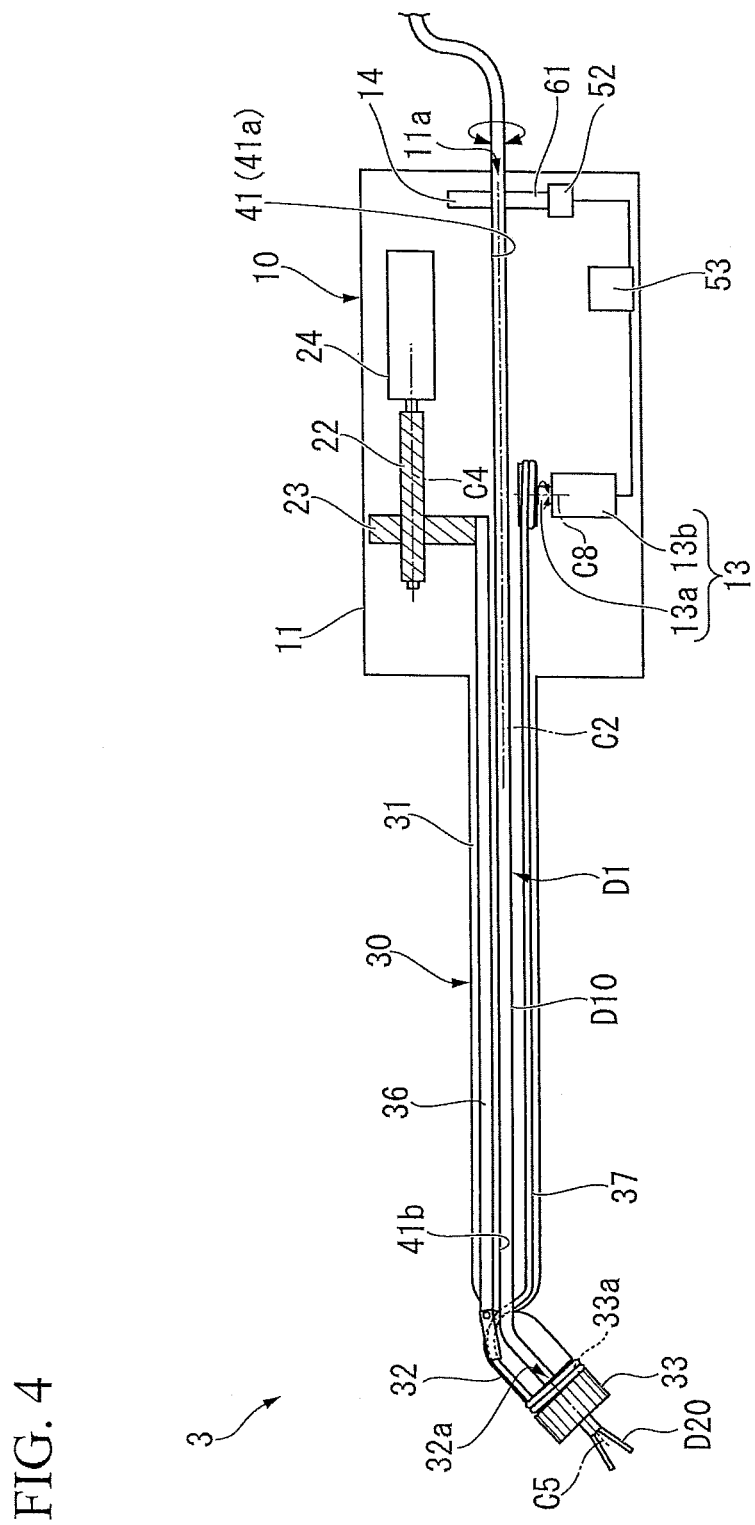
FIG. 4 is a cross-sectional view of schematic main parts in a plane of a medical manipulator according to a third embodiment of the present invention.

As shown in FIG. 4, a medical manipulator 3 according to the embodiment includes a body-side medical treatment tool rotating roller (proximal-end-side contact section) 61 instead of the second drive motor 51 and the body-side medical treatment tool rotating roller 12A of the medical manipulator 2 according to the second embodiment.

The body-side medical treatment tool rotating roller 61 is disposed such that the medical treatment tool insertion section D10 inserted through the body-side channel 41a is sandwiched between the body-side medical treatment tool rotating roller 61 and the above-described support roller 14. The body-side medical treatment tool rotating roller 61 is supported rotatably by the casing 11. In the embodiment, the user rotates the proximal-end side of the medical treatment tool insertion section D10 about the axis C2 of the channel 41. At this time, the body-side medical treatment tool rotating roller 61 and the support roller 14 are configured to rotate without slipping with respect to the medical treatment tool insertion section D10.

The memory of the drive amount control section 53 stores a constant representing the necessary number of rotations of the output shaft 13a of the drive motor 13 when the body-side medical treatment tool rotating roller 61 rotates one rotation so that the amount of rotational movement in which the user rotates the proximal-end side of the medical treatment tool insertion section D10 is equal to the amount of rotational movement in which the rotation member 33 rotates about its own axis C5.

The calculation element performs a calculation operation of multiplying the detection result transmitted from the encoder 52 by the above-described constant, applies a voltage according to the calculation result to the drive motor 13, and rotates the rotation member 33 according to the drive motor 13.

According to the medical manipulator 3 according to the embodiment, it is possible to rotate the distal-end side similarly to the proximal-end side of the flexible medical treatment tool D1 inserted through the channel 41 when the proximal-end side of the flexible medical treatment tool D1 is rotated.

Further, it is possible to have an advantageous effect similar to that of the above-described embodiment even though the medical manipulator 2 according to the second embodiment is configured without the second drive motor 51 and has a spec in which the proximal-end side of the medical treatment tool D1 is manually rotated. Thereby, it is possible to reduce the manufacturing cost of the medical manipulator 3.

The user can intuitively perform a rotation operation by operating the proximal-end side of the medical treatment tool insertion section D10.

(Fourth Embodiment)

Next, the fourth embodiment of the present invention will be described with reference to FIG. 5. The same portions as those of the above-described embodiment are assigned the same reference signs, a description thereof will be omitted, and only different points will be described.

Figure 5:
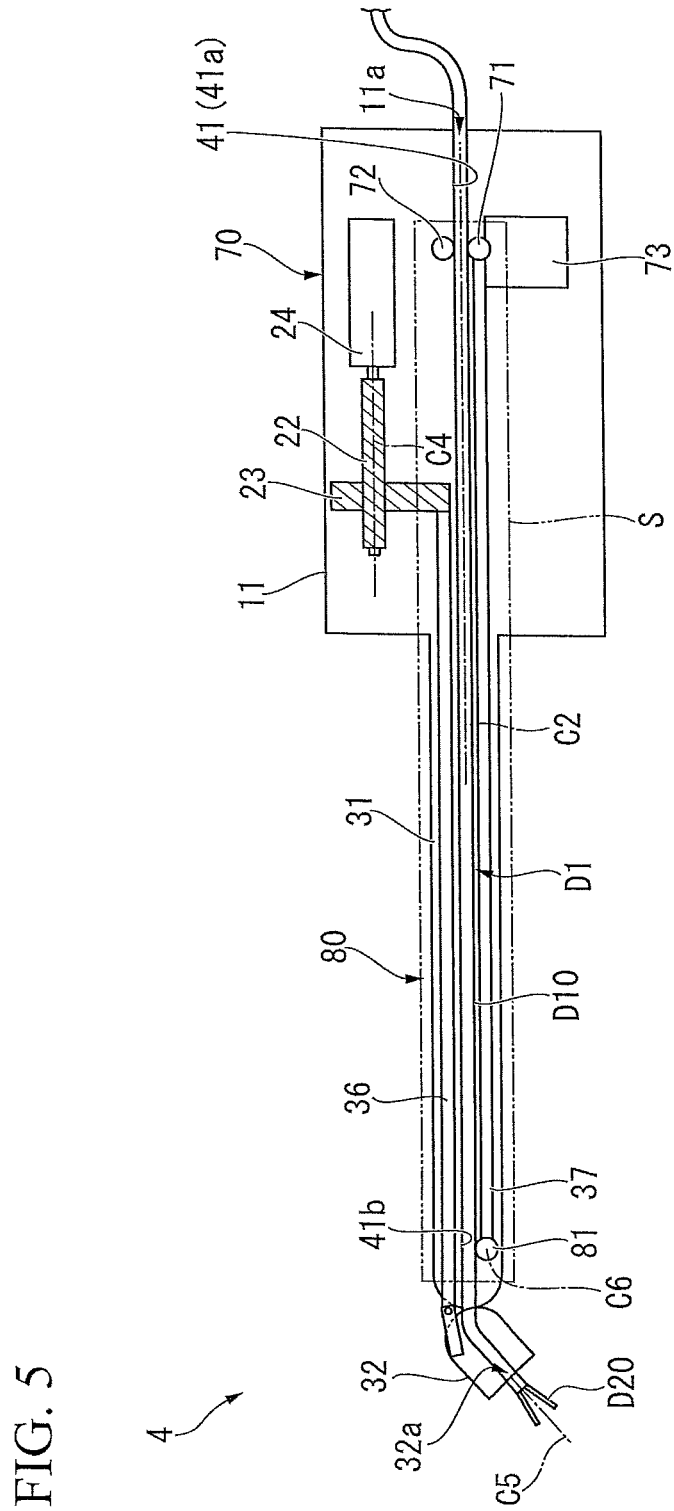
FIG. 5 is a cross-sectional view of schematic main parts in a plane of a medical manipulator according to a fourth embodiment of the present invention.

As shown in FIG. 5, a medical manipulator 4 according to the embodiment includes a body section 70 and an insertion section 80. The insertion section 80 is formed to be more elongate than the body section 70 and has a proximal-end portion connected to the body section 70.

The body section 70 includes a body-side medical treatment tool moving roller (proximal-end-side contact section and movement amount detection section) 71, a support roller 72, and a drive motor (first drive section, second drive section) 73 instead of the support roller 14, the body-side medical treatment tool rotating roller 61, the encoder 52, the drive amount control section 53, and the drive motor 13 provided in the body section 10 in the medical manipulator 3 according to the third embodiment.

The body-side medical treatment tool moving roller 71, the support roller 72, and the drive motor 73 are housed in the casing 11.

The body-side medical treatment tool moving roller 71 and the support roller 72 are disposed to rotate on a reference plane S including the axis C2 of the channel 41 and supported by the casing 11. The body-side medical treatment tool moving roller 71 and the support roller 72 are disposed such that the medical treatment tool insertion section D10 of the medical treatment tool D1 which is inserted through the body-side channel 41a is sandwiched therebetween. An engagement shaft (not shown) is provided to protrude on an axis of the body-side medical treatment tool moving roller 71 and the proximal-end side of the operation wire 37 is wound around the engagement shaft.

Although not shown, the output shaft of the drive motor 73 is fixed to the body-side medical treatment tool moving roller 71. A motor body for generating a driving force and transferring the driving force to the output shaft is fixed to the casing 11.

The drive motor 73 can rotate the body-side medical treatment tool moving roller 71 in a desired direction on the reference plane S.

The medical treatment tool insertion section D10 of the medical treatment tool D1 inserted through the body-side channel 41a is in contact with the side surface of the body-side medical treatment tool moving roller 71 and the side surface of the support roller 72.

The insertion section 80 consists of the insertion-section body 31 and the swing member 32 according to the first and second embodiments.

In the embodiment, an insertion-side medical treatment tool moving roller (distal-end-side contact section) 81 is disposed on the distal-end section of the insertion-section body 31. The insertion-side medical treatment tool moving roller 81 is disposed to rotate on the above-described reference plane S and supported rotatably by the insertion-section body 31. An engagement shaft (not shown) is protrusively provided on an axis of the insertion-side medical treatment tool moving roller 81. The proximal-end side of the operation wire 37 is wound around the engagement shaft.

The medical treatment tool insertion section D10 of the medical treatment tool D1 inserted through the insertion-side channel 41b is in contact with a side surface of the insertion-side medical treatment tool moving roller 81.

An outer diameters of the body-side medical treatment tool moving roller 71 and an outer diameters of the insertion-side medical treatment tool moving roller 81 are set to be equal to each other. In addition, the outer diameter of the engagement shaft of the body-side medical treatment tool moving roller 71 and an outer diameter of the engagement shaft of the insertion-side medical treatment tool moving roller 81 are set to be equal to each other.

When the drive motor 73 rotates the body-side medical treatment tool moving roller 71, the insertion-side medical treatment tool moving roller 81 rotates by transferring the driving force via the operation wire 37. At this time, the body-side medical treatment tool moving roller 71 and the insertion-side medical treatment tool moving roller 81 rotate at the same speed. The speeds (circumferential speeds of the body-side medical treatment tool moving roller 71 and the insertion-side medical treatment tool moving roller 81) at which the body-side medical treatment tool moving roller 71 and the insertion-side medical treatment tool moving roller 81 move the medical treatment tool insertion section D10 in the direction of the axis C2 of the medical treatment tool D1 are equal to each other.

That is, in the embodiment, the amount of movement of the medical treatment tool D1 with respect to the channel 41 is an amount of movement (hereinafter referred to as an "amount of forward/backward movement") of the direction of the axis C2 of the medical treatment tool Dl. The body-side medical treatment tool moving roller 71 and the insertion-side medical treatment tool moving roller 81 function as a drive amount adjustment section.

According to the medical manipulator 4 according to the embodiment, the distal-end side of the medical treatment tool D1 can also be moved in the direction of the axis C2 of the medical treatment tool D1 similarly to the proximal-end side of the flexible medical treatment tool D1 inserted through the channel 41 when the proximal-end side of the flexible medical treatment tool D1 is moved in the direction of the axis C2 of the medical treatment tool D1.

The medical treatment tool insertion section D10 is possible to move in the direction of the axis C2 of the medical treatment tool Dl when the insertion-side treatment instrument moving roller 81 is rotated about its own axis C6, as the result, an amount of protrusion of the treatment section D20 protruding from the insertion section 80 is possible to adjust automatically.

Figure 6:
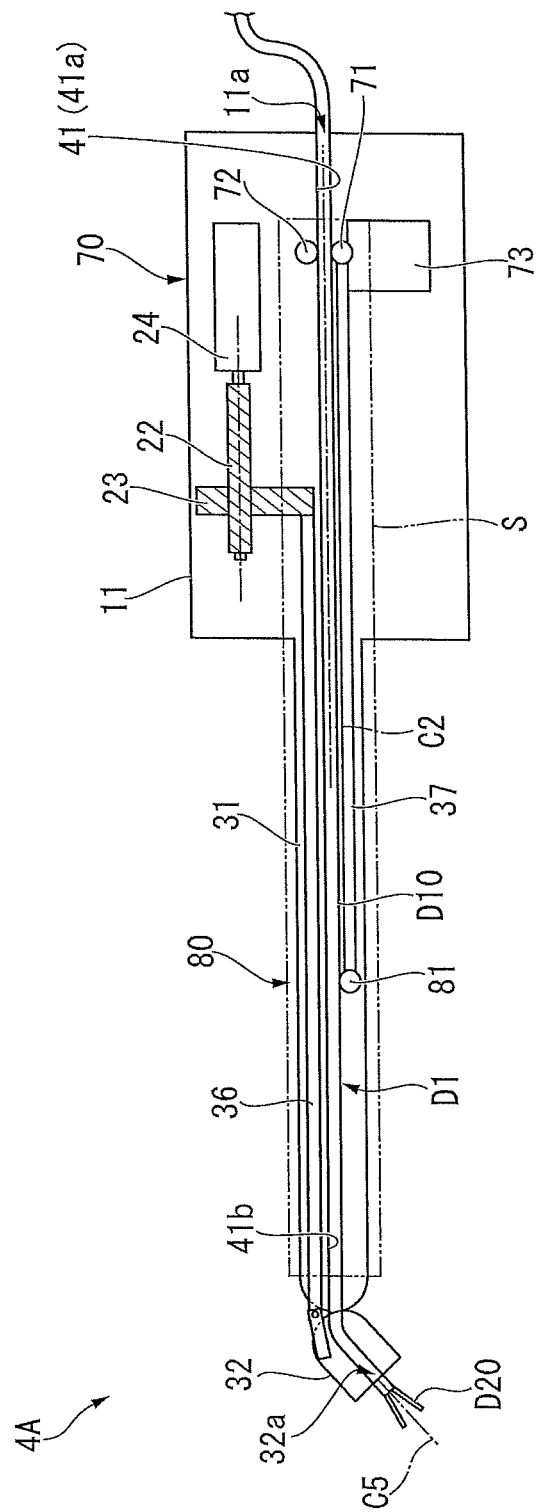
FIG. 6 is a cross-sectional view of schematic main parts in a plane of a medical manipulator according to a modified example of the fourth embodiment of the present invention.

In the embodiment, the insertion-side medical treatment tool moving roller 81 is configured to be disposed on the distal-end section of the insertion-section body 31. However, if the insertion-side medical treatment tool moving roller 81 is disposed in the insertion section 80, a position of the insertion-side medical treatment tool moving roller 81 is not particularly limited. For example, as in a medical manipulator 4A shown in FIG. 6, the insertion-side medical treatment tool moving roller 81 may be disposed at a middle portion in the longitudinal direction in the insertion-section body 31 or within the swing member 32.

In the embodiment, an operation of moving the proximal-end side of the medical treatment tool D1 in the direction of the axis C2 and an operation of moving the distal-end side of the medical treatment tool D1 in the direction of the axis C2 of the medical treatment tool D1 may be performed using different motors. A configuration in which the operation of moving the proximal-end side of the medical treatment tool D1 in the direction of the axis C2 of the medical treatment tool D1 is performed by the user and the medical manipulator detects the amount of forward/backward movement of the proximal-end side of the medical treatment tool D1 moved by the user to move the distal-end side of the medical treatment tool D1 by the same amount of forward/backward movement as that of the proximal-end side of the medical treatment tool D1 in the direction of the axis C2 of the medical treatment tool D1 may be used.

While the first to fourth embodiments of the present invention have been described illustrated above, it should be understood that these are exemplary of the invention and are not to be considered as limiting. Additions, omissions, substitutions, and other modifications can be made without departing from the spirit or scope of the present invention.

Figure 7:
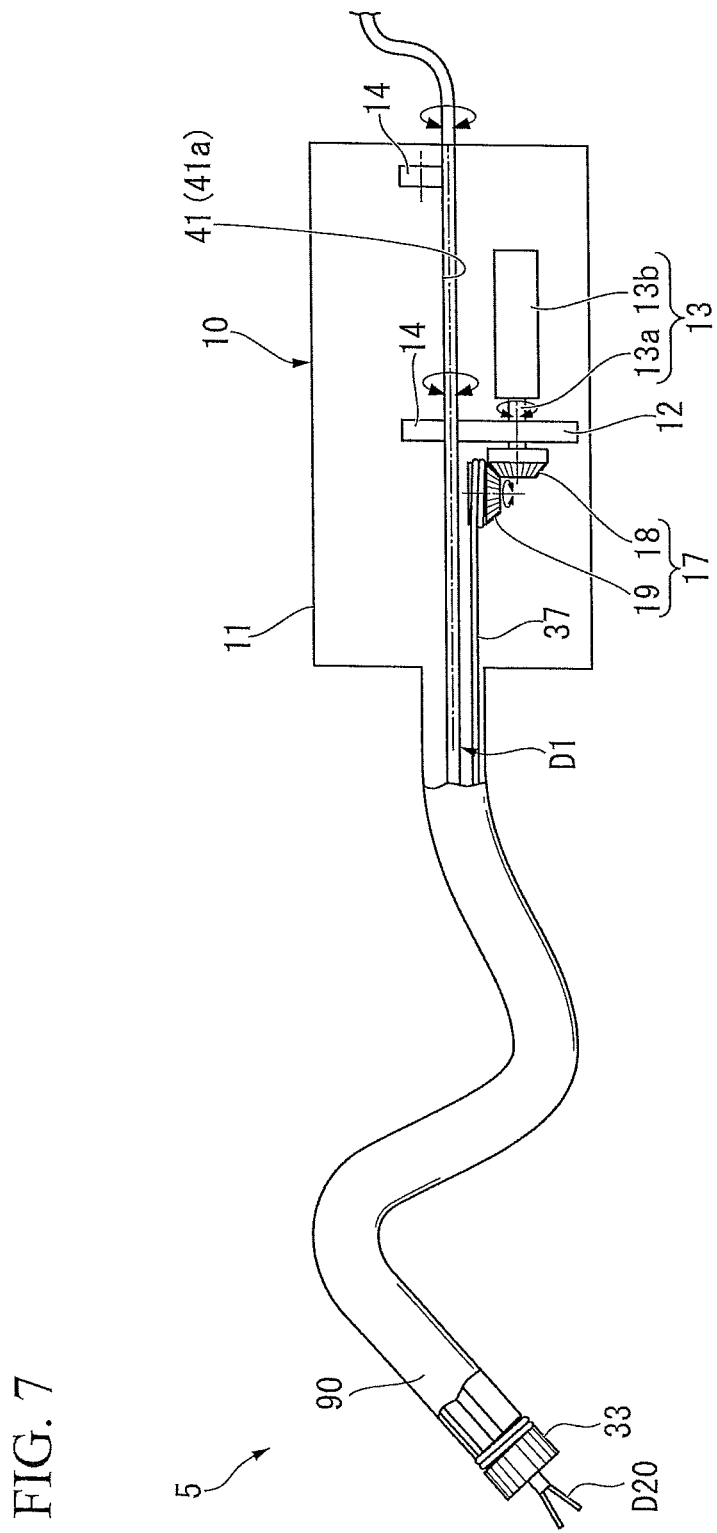
FIG. 7 is a perspective view of a medical manipulator in a modified example of the embodiment of the present invention.

For example, as in a medical manipulator 5 shown in FIG. 7, an insertion section 90 in the medical manipulator 1 may be formed of a flexible material such as a resin to have flexibility. Even in this case, it is possible to have an advantageous effect similar to that of the first embodiment by detecting an amount of rotational movement of the proximal-end side of the medical treatment tool D1 and causing the rotation member 33 to rotate the distal-end side of the medical treatment tool D1 by the amount of rotational movement. Likewise, it is possible to use the flexible insertion section even in the other embodiments.

In addition, in the above-described first to fourth embodiments, a process of detecting either one of the amount of rotational movement and the amount of forward/backward movement of the proximal-end side of the medical treatment tool D1 has been described. However, both a configuration in which the amount of rotational movement is detected and a configuration in which the amount of forward/backward movement is detected may be configured to be included in the medical manipulator and the distal-end side of the medical treatment tool D1 may be configured to be moved by a detected amount of movement by performing switching to detect either one of the amount of rotational movement and the amount of forward/backward movement.

In the above-described first to fourth embodiments, the support rollers 14 and 72 are not essential components. This is because it is possible to have a similar advantageous effect even when rollers are arranged so that one roller pushes the medical treatment tool insertion section D10 to an inner circumferential surface of the channel 41.

In the above-described first to third embodiments, a plurality of rotation members 33 may be configured to be included. In this case, the rotation members 33 are configured to be wound and mounted at a plurality of positions in the direction of the axis C2 of the operation wire 37.

Even in the fourth embodiment, a plurality of insertion-side medical treatment tool moving rollers 81 may be configured to be included.

What is claimed is:

1. A medical manipulator comprising:
   a body;
   an elongate insertion section having a proximal-end portion connected to the body;
   a channel through which a flexible medical treatment tool is able to be inserted, the channel being configured to communicate with a distal-end opening formed in a distal-end section of the insertion section and to communicate with a proximal-end opening formed in the body;
   a movement amount detection section configured to detect an amount of movement of the medical treatment tool inserted through a body-side portion of the channel, the body-side portion of the channel being a portion of the channel provided in the body;
a distal-end-side contact section provided to be in contact with the medical treatment tool inserted through an insertion-side portion of the channel, the insertion-side portion of the channel being a portion of the channel provided in the insertion section, the distal-end-side contact section being configured to rotate about its own axis to move the medical treatment tool to the insertion-side channel;
a first drive section provided on the body section, the first drive section being configured to rotate the distal-end-side contact section, and
a wire configured to rotate the distal-end-side contact section;
wherein the first drive section has an output shaft configured to rotate to transfer a driving force;
the wire is wound around the output shaft and connected to the distal-end-side contact section; and
the distal-end-side contact section is rotated so as to move the medical treatment tool with respect to the insertion-side channel by an amount of movement which is a same amount of movement as an amount of movement detected by the movement amount detection section.

2. The medical manipulator according to claim 1, further comprising:
a proximal-end-side contact section which is capable of contacting with the medical treatment tool inserted through the body-side channel and which rotates about its own axis to move the medical treatment tool with respect to the body-side channel,
wherein the first drive section rotates the proximal-end-side contact section.

3. The medical manipulator according to claim 2, further comprising:
an output branch mechanism configured to transfer part of the driving force about an axis of the output shaft as a driving force about the axis of an auxiliary output shaft intersecting the axis of the output shaft,
wherein the output shaft is disposed in parallel to an axis of the channel,
the wire is wound around the auxiliary output shaft and connected to the distal-end-side contact section,
the amounts of movement are amounts of movement about the axis of the channel,
an axis of the proximal-end-side contact section is disposed in parallel to the axis of the channel, and
the proximal-end-side contact section is rotated by the driving force transferred to the output shaft.

4. A medical manipulator comprising:
a body;
an elongate insertion section having a proximal-end portion connected to the body;
a channel through which a flexible medical treatment tool is able to be inserted, the channel being configured to communicate with a distal-end opening formed in a distal-end section of the insertion section and to communicate with a proximal-end opening formed in the body;
a movement amount detection section configured to detect an amount of movement of the medical treatment tool inserted through a body-side portion of the channel, the body-side portion of the channel being a portion of the channel provided in the body;
a distal-end-side contact section provided to be in contact with the medical treatment tool inserted through an insertion-side portion of the channel, the insertion-side portion of the channel being a portion of the channel provided in the insertion section, the distal-end-side contact section being configured to rotate about its own axis to move the medical treatment tool to the insertion-side channel;
a first drive section provided on the body section, the first drive section being configured to rotate the distal-end-side contact section,
a proximal-end-side contact section capable of contacting with the medical treatment tool inserted through the body-side channel, the proximal-end-side contact section rotating about its own axis to move the medical treatment tool with respect to the body-side channel;
a second drive section provided on the body section, the second drive section being configured to rotate the proximal-end-side contact section; and
a drive amount adjustment section for adjusting a drive amount of the first drive section for rotating the distal-end-side contact section based on a result of detecting the amount of movement,
wherein, the distal-end-side contact section is rotated so as to move the medical treatment tool with respect to the insertion-side channel by an amount of movement which is a same amount of movement as an amount of movement detected by the movement amount detection section; and
when the proximal-end-side contact section is rotated by the second drive section, the movement amount detection section transmits the result of detecting the amount of movement to the drive amount adjustment section and the drive amount adjustment section adjusts the drive amount of the first drive section based on the detection result such that the amount of movement of the medical treatment tool with respect to the insertion-side channel is equal to the amount of movement of the medical treatment tool with respect to the body-side channel that has been detected by the movement amount detection section.

5. The medical manipulator according to claim 1, wherein the amounts of movements are an amount of movement in an axial direction of the channel, and the distal-end-side contact section is disposed so as to rotate on a reference plane including the axis of the channel, the distal-end-side contact section is rotated so as to move the medical treatment tool with respect to the insertion-side channel by an amount of movement which is a same amount of movement as an amount of movement detected by the movement amount detection section.

6. The medical manipulator according to claim 1,
wherein the amounts of movements are an amount of rotation about the axis of the channel, and
the distal-end-side contact section is disposed so as to rotate about an axis parallel to the axis of the channel.

* * * * *